United States Patent [19]

Trescony et al.

[11] Patent Number: 5,919,472
[45] Date of Patent: Jul. 6, 1999

[54] TREATMENT OF ALDEHYDE-FIXED TISSUE

[75] Inventors: Paul V. Trescony, Champlin, Minn.;
Peter Zilla, Cape Town, South Africa

[73] Assignee: Medtronic, Inc., Minneapolis, Minn.

[21] Appl. No.: 08/619,843

[22] Filed: Mar. 19, 1996

[51] Int. Cl.$^6$ .................................................. A61F 13/00
[52] U.S. Cl. ............................................. 424/422; 424/400
[58] Field of Search ........................ 623/1, 2, 3; 424/422

[56] References Cited

U.S. PATENT DOCUMENTS

| | | | |
|---|---|---|---|
| 4,786,287 | 11/1988 | Nashef et al. ........................... | 8/94.21 |
| 5,188,834 | 2/1993 | Grimm et al. .......................... | 424/422 |
| 5,460,797 | 10/1995 | Ryan ...................................... | 435/40.5 |

*Primary Examiner*—Jose' G. Dees
*Assistant Examiner*—Kathryne E. Shelborne
*Attorney, Agent, or Firm*—Harold R. Patton; Peter Forrest

[57] ABSTRACT

A method of preparing a biological tissue for implantation that has been treated with an aldehyde, the method utilizing a cyclic nonpeptidyl amide-functional and/or imide-functional compound to remove excess aldehyde from the treated biological material, thereby detoxifying the biological tissue.

20 Claims, No Drawings

TREATMENT OF ALDEHYDE-FIXED TISSUE

FIELD OF THE INVENTION

This invention relates to a method of treating aldehyde-treated, particularly aldehyde-fixed biological material, such as heart valves, to reduce residual aldehyde levels.

BACKGROUND OF THE INVENTION

The implantation of biological materials, in particular those which are collagenous, is common in a number of medical applications. These applications include implantation of heart valves, pericardium, arteries, veins, skin, tendons, ligaments etc. The biological materials may be harvested from the same individual (autologous), from a different species (heterologous), or from the same species but from a different individual (homologous).

Without any prior treatment, implanted collagenous biological material that is heterologous or homologous may be regarded as a foreign antigen and trigger a host immune response that destroys the biological material. Treating the biological material with aldehydes such as formaldehyde, glutaraldehyde, glyoxal, or dialdehyde starch serves to: 1) enhance the mechanical durability and resistance to proteolytic attack by crosslinking collagen within the biological material; 2) greatly reduce an immune response to the implant by combining with and masking antigenic sites within the tissue; and 3) maintain sterility prior to implantation. Such aldehyde-treated material is termed "fixed."

While treatment with aldehydes prevents the triggering of an immune response and subsequent rejection of the biological material, residual aldehydes are known to be slowly released from aldehyde-treated biological materials and are known to be cytotoxic. The release of cytotoxic aldehyde related products can cause a local inflammatory response and can prevent complete healing of the implant. The customary method of briefly washing the aldehyde-fixed implant with sterile saline or water just prior to implantation cannot completely remove excess aldehyde within the fixed tissue because of diffusion limitations and because a substantial amount of aldehyde is released from the implant by slow hydrolysis over a long period of time. This limitation is particularly emphasized in thick aldehyde-fixed biological materials, such as stentless heart valves, vascular grafts, ligaments, and the like. Other methods are therefore necessary to further eliminate residual aldehydes thus "detoxifying" the fixed biological material.

One method of removing aldehyde residues is by using an aminodicarboxylic acid such as glutamic acid or aspartic acid as disclosed in U.S. Pat. No. 4,120,649 (Schechter). In addition to aminodicarboxylic acid, primary and secondary amines may be used singly or in combination to effect aldehyde removal as disclosed in U.S. Pat. No. 4,786,287 (Nashef et al.). The preferred amine is a primary amine having a general formula, R—NH$_2$, where R can be an aliphatic, aromatic or a combination thereof which may be dissolved in a rinsing solution or immobilized on a solid support. The rinsing solution is buffered to a pH of 7.0 to 7.6. Because of the high pH of the rinsing solution, elevated temperatures and continuous rinsing or many rinsings are needed to promote efficient diffusion of the aldehyde from the tissue. This method, however, does not satisfactorily remove all the aldehydes within the tissue. For example, residual aldehyde remains at a level that prevents a cell lining from growing on the surface of thick-walled tissue.

A method disclosed in U.S. Pat. No. 5,188,834 (Grimm et al.) provides improvement over the aminodicarboxylic acid and amine treatment methods described above by using a dicarboxylic acid in an acidic medium with a pH of 2.5 to 5.5. At this lower pH, there is an enhanced degradation of tissue-bound polymeric aldehyde species to low molecular weight diffusable species. The low molecular weight species can more readily react with the dicarboxcylic acids and be removed from the tissue by diffusion. Grimm's method requires, however, that the aldehyde detoxified tissue be stored in a separate nonaldehyde containing storage solution. The storage solution typically contains two cytostatic agents, methyl and propyl paraben.

Thus, what is needed is another method for treating aldehyde-treated material, particularly thick tissue, in order to effectively remove residual traces of aldehyde from the material, and preferably, to provide a storage solution with improved bacteriocidal and fungicidal activity.

SUMMARY OF THE INVENTION

The invention uses a preparation method combining cyclic nonpeptidyl amide-functional and/or imide-functional compounds, preferably in a low pH medium, with aldehyde-treated biotissue, which is generally of a collagenous material. The method is particularly advantageous for treating thick walled (greater than 1 mm) tissue.

Specifically, the present invention provides a method for preparing a biological tissue for implantation, comprising: treating a biological tissue with an aldehyde; and treating the aldehyde-treated biological tissue with a cyclic nonpeptidyl compound having at least one amide or imide group in an aqueous treatment medium having a pH of less than about 10. These steps can be carried out substantially simultaneously or sequentially. If they are carried out sequentially, the tissue is generally fixed (i.e., crosslinked) by the aldehyde and the residual aldehyde is subsequently detoxified. If the steps are carried out simultaneously, the treated tissue supports cell growth, but may or may not be "fixed" as herein defined.

The cyclic nonpeptidyl compound is preferably a cyclic nitrogen metabolite or a synthetic heterocycle. A preferred group of such compounds includes uridine, uracil, thymidine, thymine, 5,6-dihydroxyuracil, 5,6-dihydroxythymine, inosine, hypoxanthine, xanthine, xanthosine, uric acid, allantoin, guanine, guanosine, nicotinamide, orotic acid, urazole, glycoluril, hydantoin, 5,5-dimethyl hydantoin, pyrrolid-2-one, pyrazol-3-one, imidazol-2-one, allopurinol, and theobromine.

Preferably, the cyclic nonpeptidyl compound has both amide and imide groups. A preferred group of such compounds includes uric acid, allantoin, urazole, uridine, thymidine, uracil, thymine, 5,6-dihydroxyuracil, 5,6-dihydroxythymine, orotic acid, xanthine, xanthosine, hydantoin, 5,5-dimethylhydantoin, and theobromine.

DETAILED DESCRIPTION OF THE INVENTION

The present invention provides a method for detoxifying aldehyde-treated tissues, preferably aldehyde-fixed tissues. That is, the method of the present invention can be used to reduce residual aldehyde levels in bioprosthetic tissue (also referred to herein as biological tissue or biotissue) prior to surgical implantation of the tissue. The method uses cyclic nonpeptidyl compounds containing at least one amide (—C(O)NH—) group, at least one imide (—C(O)NH—C(O)—) group, or both, referred to herein as an amide/imide compound. This method is particularly effective for thick walled tissue, i.e., tissue greater than about 1 mm thick. Advantageously, the cyclic nonpeptidyl amide- and/or imide-functional compounds can be used simultaneously with the aldehydes to provide treated tissue capable of supporting cell growth. Furthermore, a solution containing an aldehyde and a cyclic nonpeptidyl amide/imide compound can be used as an antimicrobial storage media.

The tissue is first extracted from its source, e.g., a donor such as an animal, and typically processed by one of many conventional procedures used to prepare biological tissue for implantation as bioprosthetic material. Treatment of extracted biological tissue with aldehyde compounds is well known, and is described in U.S. Pat. Nos. 4,120,649 (Schechtter), 3,988,782 (Dardick et al.), and 4,553,974 (Dewanjee). Glutaraldehyde is the preferred fixing agent, although other suitable aldehydes can be used including, for example, formaldehyde, glyoxal, and dialdehyde starch. The aldehyde is used in an amount and for a time that is effective to crosslink collagen in the tissue to a degree sufficient to stabilize the tissue and to render it substantially nonantigenic. Such tissue is referred to as aldehyde-fixed tissue or simply "fixed" tissue.

In the method of the present invention, aldehyde-treated tissue is further treated with a cyclic nonpeptidyl compound containing at least one amide (—C(O)NH—) group, at least one imide (—C(O)NH—C(O)—) group, or both, in an aqueous medium having a pH of no greater than about 10. The method of the present invention is advantageous because it can effectively detoxify aldehyde-fixed tissue in no greater than about 7 days, and preferably in no greater than about 4 days.

The detoxification method of the present invention is preferably carried out in an aqueous medium having a pH of less than about 7, and more preferably in an aqueous medium having a pH of about 3–5. Preferably, for detoxification in no greater than about 7 days, the method of the present invention is carried out in an aqueous medium at a temperature greater than about 25° C., and more preferably at a temperature of about 30–45° C., although temperatures as low as 4° C. can also be used.

The extent of detoxification, i.e., removal, of aldehyde residue in tissue, such as a heart valve tissue, may be assessed in in vitro studies by endothelial cell seeding onto the tissue. Growth of an endothelial cell monolayer directly on top of the fixed and detoxified tissue provides a sensitive biological indicator that amides and/or imides have reduced the number of residual aldehydes in the tissue. Endothelial cell growth indicates that cytotoxic aldehydes are absent within the tissue.

Both the mixture of products resulting from aldehyde fixation of biological tissue and from the reaction of cyclic nonpeptidyl amide and/or imide reagents with these aldehyde products are expected to be complex. It is expected that residual Schiff's bases and other hydrolytically unstable unsaturated compounds will remain in the tissue after this treatment. Thus, it may be beneficial to treat the detoxified tissue subsequently with a reducing agent, such as sodium borohydride, to convert unstable unsaturated compounds to stable saturated ones. This can generally be done to aldehyde-treated tissue, such as glutaraldehyde-fixed aortic wall tissue, without significantly altering the favorable detoxification achieved with cyclic nonpeptidyl amides and/or imides.

A preferred group of cyclic nonpeptidyl amide-functional and/or imide-functional compounds suitable for use in the method of the present invention can be represented generally by the formulae R—C(O)—NH—R' and R—C(O)—NH—C(O)—R', wherein R and R' independently represent H, alkyl and alkenyl groups (having 1 or more carbon—carbon double bonds) optionally substituted with oxygen atoms, nitrogen atoms, carbonyl groups, amino groups, amido groups, and hydroxyl groups. The compounds preferably contain 1–3 five or six membered rings. More preferably, R and R' together with —C(O)—NH— or —C(O)—NH—C(O)— form a ring or rings. Most preferably, the amide and/or imide groups are part of a ring, as opposed to pendant therefrom. Also, it is preferred that the compounds be water soluble.

Suitable such compounds may be grouped into two categories of compounds. Group I are cyclic nitrogen metabolites including, for example, uridine, uracil, thymidine, thymine, 5,6-dihydroxyuracil, 5,6-dihydroxythymine, inosine, hypoxanthine, xanthine, xanthosine, uric acid, allantoin, guanine, guanosine, nicotinamide, and orotic acid. Group II are synthetic heterocyclics including, for example, urazole, glycoluril, hydantoin, 5,5-dimethyl hydantoin, pyrrolid-2-one, pyrazol-3-one, imidazol-2-one, allopurinol, barbituric acid, and theobromine.

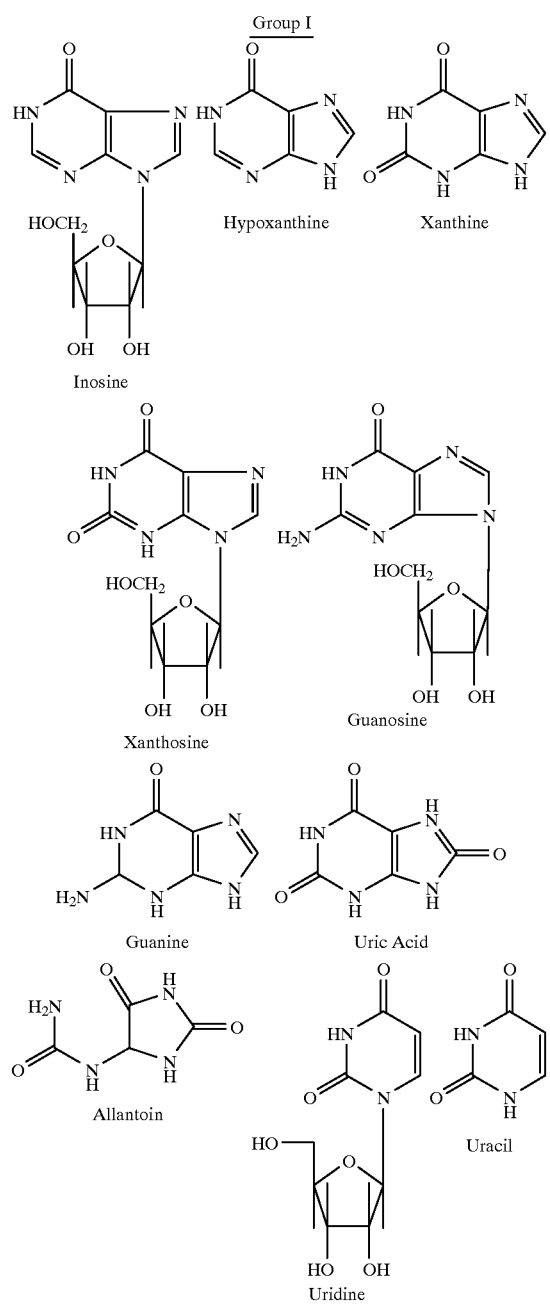

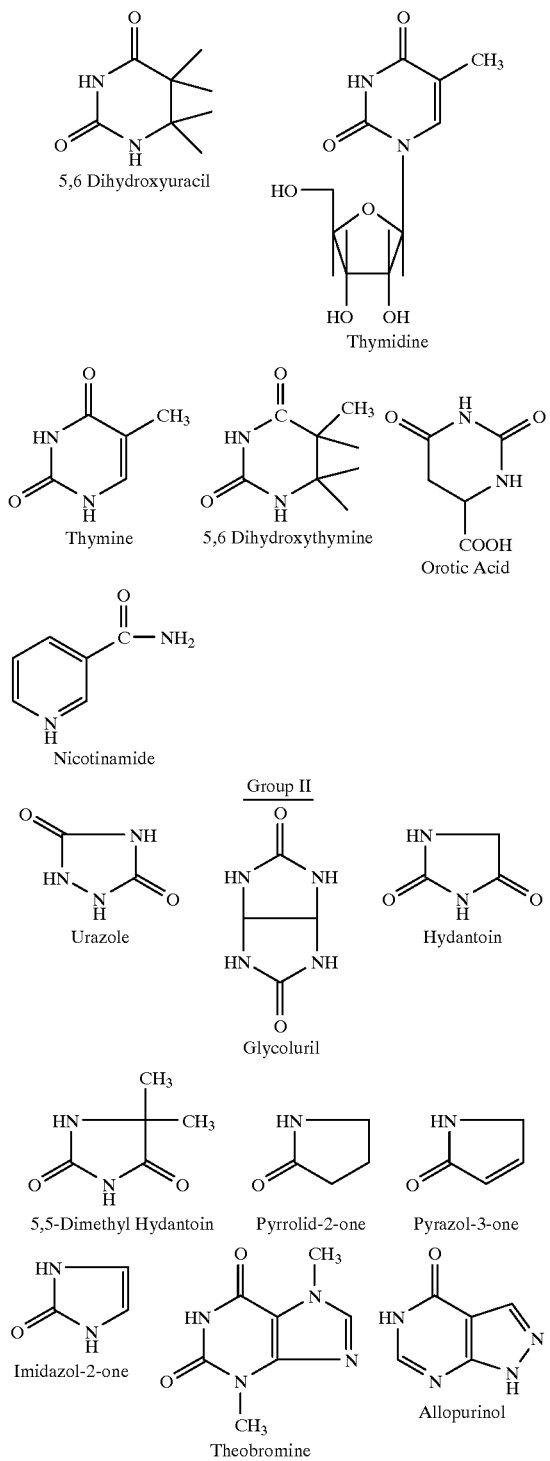

A preferred group of compounds suitable for use in the method of the present invention include those compounds with an imide group, and a more preferred group of compounds are those with both an amide group and an imide group. This includes uric acid, allantoin, urazole, uridine, thymidine, uracil, thymine, 5,6-dihydroxyuracil, 5,6-dihydroxythymine, orotic acid, xanthine, xanthosine, hydantoin, 5,5-dimethylhydantoin, and theobromine. Another preferred group of compounds are those that are natural mammalian metabolites, e.g., purine or pyrimidine metabolites. This includes uridine, thymidine, uracil, thymine, 5,6-dihydroxyuracil, and 5,6-dihydroxythymine, orotic acid, xanthine, xanthosine, uric acid, allantoin, and nicotinamide. A more preferred group are those compounds that are natural metabolites and have both an amide group and an imide group. A particularly preferred group of compounds are hypoxanthine, allantoin, barbituric acid, and urazole. One other compound that is useful as a detoxifying compound and is a natural mammalian metabolite, but is not cyclic, is urea.

An advantage of the present invention is that the amide-functional and/or imide-functional compounds, particularly those that are natural metabolites, have generally low toxicity, so that the biotissue can be implanted directly after the amide/imide treatment. After the amide/imide treatment, however, it is desirable to rinse the tissue with a sterile saline solution prior to implantation.

Furthermore, using amide-functional and/or imide-functional compounds as detoxifying agents, the detoxification step can be carried out substantially simultaneously with the aldehyde-treatment step. That is, aldehydes, such as those used in typical fixation methods, and amide/imide compounds as described herein can be combined in one medium and used to contact the biotissue to both treat the biotissue such that it will support cell growth, whether or not it has been crosslinked or "fixed." Furthermore, because products of glutaraldehyde and nitrogen-containing compounds, such as amides and imides, exhibit antimicrobial activity (see, for example, U.S. Pat. No. 4,454,133 (Berke et al.), the biotissue can be stored in the amide/imide treatment solution for long periods of time. Thus, the amide/imide detoxifying agents described herein can be added to an aldehyde solution during fixation effecting a "one-pot" fixation, detoxification, and sterilization/storage procedure.

The volume of the amide/imide treatment solution, the concentration of the amide/imide, and the number and duration of rinses used in the method of the present invention can vary, depending on the type of tissue, the residual aldehyde concentration in the tissue, the temperature and pH of the treatment solution, etc. Generally, it is desirable to have a stoichiometric excess of the amide/imide groups over the releasable aldehyde groups. Preferably, about a five-fold excess is used, and more preferably about a 100-fold excess is used. Typically, effective amide/imide concentrations are about 0.01 M to about 0.1 M. The amide/imide can be dissolved completely in the treatment solution, it can be dispersed therein without complete dissolution, or it can also be attached to a solid support.

Biological tissue that can be detoxified using this method is any tissue that can be fixed with an aldehyde such as glutaraldehyde. This includes, for example, epithelial or fibrous connective tissue, such as pericardial tissue, dura mater, fascia lata, amnion, tendon, ligament, cartilage, arteries, veins, skin patches, bone, heart valves, reconstituted collagen, etc. This method is particularly well suited for thick and/or dense biological tissues, such as heart valves, which are particularly difficult to detoxify.

The invention has been described with reference to various specific and preferred embodiments and will be further described by reference to the following detailed examples. It is understood, however, that there are many extensions, variations, and modification on the basic theme of the present invention beyond that shown in the examples and detailed description, which are within the spirit and scope of the present invention.

EXAMPLES

Harvesting and Fixation of Porcine Aortic Wall Tissue

Aortas from large pigs were roughly dissected at the abatoir and transported to the laboratory in Hank's Balanced Salt Solution (HBSS) containing the following antibiotics: Amphotericine B, 25 μg/ml; Clindamycine Phosphate, 120 μg/ml; Vancomycine, 50 μg/ml; and Polymyxine B, 130 μg/ml. After dissecting fatty and connective tissue from the aortas in the laboratory 1.2 cm diameter discs were punched from the aortic wall and stored in fresh Hanks Balanced Salt Solution (HBSS) with antibiotics at 4° C. for up to 2 days.

The aortic wall discs were fixed by placing in 0.2% glutaraldehyde (GA) in Phosphate Buffered Saline (PBS) at 4° C. for 7 days with 10 ml of fixative per disc. The discs were then placed in PBS containing 0.2% GA and 1.0% isopropanol at 4° C. for 3½ hours with 10 ml of solution per disc. The discs were then placed in sterile PBS alone at 37° C. for 24 hours with 10 ml of PBS per disc.

Preparation of Detoxifying Compounds

The following detoxifying compounds were prepared as described below at room temperature (25–30° C.) unless otherwise noted and then sterilized by 0.2 μm filtration.

0.1 M allantoin (ALAN): 16.3 g of ALAN was added to 800 ml of 0.625 M acetic acid heated to 40° C. and titrated to pH 4.5 with 1 N NaOH and made up to 1 liter total volume with water.

0.02 M hypoxanthine (HYPX): 2.7 g of HYPX was added to 640 ml of 0.625 M acetic acid, heated to 40° C., titrated to pH 4.5 with 1 N NaOH and made up to 1 liter total volume with water.

0.1 M urazole (URAZ): 10.1 g of URAZ was added to 800 ml of 0.625 M acetic acid, titrated to pH 4.5 with 1.0 N NaOH, and made up to 1 liter total volume with water.

0.1 M barbituric acid (BBA): 12.8 g of BBA was added to 640 ml of 0.625 M acetic acid, titrated to pH 4.5 with 0.1 N NaOH, and made up to 1 liter total volume with water.

0.1 M histidine (HIST): 15.5 g of HIST was added to 800 ml of 0.625 M acetic acid, titrated to pH 4.5 with 1.0 M NaOH, and made up to 1 liter total volume with water.

0.005 M 1-lysine (LYS): 0.73 g of LYS was added to 1000 ml of 0.625 M acetic acid. The solution pH was 5.75.

0.8% 1-glutamic acid (GLTA): 8.0 g of GLTA was added to 1000 ml of distilled water and stirred at 37° C. to dissolve.

Detoxification of Glutaraldehyde Fixed Tissue Discs

Glutaraldehyde fixed aortic wall discs were incubated in a sterile aqueous solution of a detoxifying compound at 37° C. for 7 days with 40 ml of solution per disc. The discs were then transferred to PBS and incubated at 4° C. for 3 days with 10 ml of PBS per disc. The discs were then attached to TEFLON framing rings in a laminar flow hood and placed in HBSS with antibiotics as described above and incubated at 37° C. for 2 days with 2 ml of solution per disc prior to endothelial cell seeding.

Post-detoxification Treatment with Sodium Borohydride

Immediately after detoxifying glutaraldehyde fixed aortic wall discs, selected discs were placed under aseptic conditions in sterile filtered 0.1 M $NaBH_3$ in PBS and incubated at 37° C. for 3 days with 40 ml of solution per disc. The discs were then attached to TEFLON framing rings in a laminar flow hood and placed in HBSS with antibiotics as described above and incubated at 37° C. for 2 days with 2 ml of solution per disc prior to endothelial cell seeding.

Combined Glutaraldehyde—Amide/Imide Treatment

Aortic wall discs were transferred under aseptic conditions from HBSS with antibiotic to 0.625 M acetic acid with 0.2% GA and 0.1 M detoxifying compound and incubated at 4° C. for 7 days with 10 ml of solution per disc. The discs were then placed in PBS containing 0.2% GA and 1.0% isopropanol and incubated at 4° C. for 3½ hours and then stored in sterile PBS alone at 4° C. for 1–2 weeks.

Endothelial Cell Seeding Experiments

Aortic wall discs (1.2 cm diameter) were attached to TEFLON framing rings and placed in 24 well tissue culture plate wells along with supplemented M199 media. Second passage human veinous endothelial cells or primary porcine aortic endothelial cells were seeded onto the tissue samples. Replicate samples were collected at several time points and processed for SEM analysis. An initial qualitative visual assessment of cell coverage and morphology was made from SEM photographs. Subsequent experiments included determination of cell number from SEM photos (1500×) where 15 areas on the seeded tissue surface were counted by 2–3 persons. The mean±1 SD was determined from 30–45 counted fields per sample.

Table 1 presents the results of in vitro seeding studies using primary cultures of porcine aortic endothelial cells or second passage human endothelial cells seeded onto glutaraldehyde-fixed tissue with or without additional detoxification. When several of the fixed tissue post-fixation treated with cyclic amide and/or imide reagents including allantoin, hypoxanthine, urazole, and barbituric acid for 7 days at 37° C. followed by three days of incubation in PBS at 4° C., cell growth was maintained over 10 days at levels comparable with treatment with amino acids including L-glutamic acid. Table 1 also shows that subsequent reduction of the fixed and detoxified tissue with sodium borohydride may in some cases be beneficial.

TABLE 1

PORCINE AORTIC ENDOTHELIAL CELL SEEDING ONTO GLUTARALDEHYDE FIXED AORTIC WALL TISSUE ± DETOXIFICATION ± $NaBH_4$ REDUCTION

| | EXPT. #1@ Cell Number × 1000 at Day 10 | | Cell Coverage at Day 10 | |
| --- | --- | --- | --- | --- |
| Detox Reagent | No $NaBH_4$ Red | +$NaBH_4$ Red. | No $NaBH_4$ Red. | +$NaBH_4$ Red. |
| allantoin | 12.3 ± 7.3 | 17.0 ± 6.5 | C⁻ | C⁻ |
| hypoxanthine | 10.5 ± 4.5 | 17.5 ± 6.8 | >50% | C⁻ |
| urazole | 20.4 ± 6.5 | 21.5 ± 7.1 | PC | C⁻ |
| barbituric acid | 5.1 ± 4.3 | 15.6 ± 3.4 | >50% | PC |
| l-glutamic acid | 15.0 ± 7.3 | 28.3 ± 6.9 | PC | PC to C⁻ |
| l-histidine | 9.9 ± 6.5 | 19.8 ± 6.2 | >50% | C⁻ |
| l-lysine | 14.5 ± 7.0 | 14.6 ± 5.2 | C⁻ | C⁻ |
| combined GTA fix + urazole | 19.1 ± 6.5* | N.D. | C | N.D. |
| barbituric acid | 6.6 ± 5.2 | N.D. | spherical/ dead | N.D. |
| No Detoxification | spherical/ dead | 7.8 ± 6.0 | spherical/ dead | 50% |
| No fixation | 5.5 ± 3.4* | N.D. | C* | N.D. |

*day 7, day 10 sample not available
@ = Experiments without additional $NaBH_4$ reduction were seeded with 2nd passage human venous endothelial cells at 125,000 cells/cm² of sample area; Experiments with additional $NaBH_4$ reduction were seeded with primary culture porcine aortic endothelial cells at 97,000 cells/cm² of sample area.
C = Confluent cell layer
PC = Preconfluent cell layer with isolated gaps between cells Table 2 shows the results of three separate additional porcine aortic endothelial cell seeding experiments comparing the detoxification effect of both amide/imide compounds with and without subsequent reduction with sodium borohydride. As with all cell seeding experiments, cell growth is a function of seeding density and the bigor of individual cell isolates. The results presented in Table 2 again show the ability of various amide/imide compounds to detoxify gluratalaldehyde fixed tissue with or without additional reduction with sodium borohydride.

TABLE 2

PORCINE AORTIC ENDOTHELIAL CELL SEEDING ONTO
GLUTARALDEHYDE FIXED AORTIC WALL TISSUE ±
DETOXIFICATION ± NaBH$_4$ REDUCTION

| Detox Reagent | EXPT. #2 seeding density 70,000 cells/cm$^2$ Cell Coverage at Day 12 | | EXPT. #3 seeding density 20,000 cells/cm$^2$ Cell Coverage at Day 12 | | EXPT #4 seeding density 50,000 cells/cm$^2$ Cell Coverage at Day 12 | |
|---|---|---|---|---|---|---|
| | No NaBH$_4$ Red. | +NaBH$_4$ Red. | No NaBH$_4$ Red. | +NaBH$_4$ Red. | No NaBH$_4$ Red. | +NaBH$_4$ Red. |
| allantoin | C$^-$ to C | C$^-$ | 60% | 80% | 75% | 80% |
| hypoxanthine | C$^-$ | C$^-$ to C | 80% | 90% | 55% | 80% |
| urazole | C$^-$ to C | C | 90% | 70% | 95% | 90% |
| 1-glutamic acid | C$^-$ | C | 90% | 85% | 85% | 90% |
| 1-histidine | C$^-$ to C | C$^-$ | 80% | 90% | 55% | 70% |
| 1-lysine | PC to C$^-$ | C | 80% | 75% | 60% | 75% |
| No Detoxification | spherical/dead | >50% to PC | spherical/dead | 50% | spherical/dead | 90% |

C = Confluent Cell Layer
PC = Preconfluent cell layer with isolated gaps between cells The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for preparing a biological tissue for implantation, comprising the ordered steps of:
    (a) a first step of treating a biological tissue with an aldehyde;
    (b) a second bioprosthesis treatment step comprising treating the aldehyde-treated biological tissue with a cyclic nonpeptidyl compound having at least one amide or imide group in an aqueous treatment medium having a pH of less than about 10, the second step following the first step.

2. The method of claim 1 wherein the aqueous treatment medium has a pH of less than about 7.

3. The method of claim 1 wherein the cyclic nonpeptidyl compound is a cyclic nitrogen metabolite or a synthetic heterocycle.

4. The method of claim 3 wherein the cyclic nonpeptidyl compound is selected from the group consisting of uridine, uracil, thymidine, thymine, 5,6-dihydroxyuracil, 5,6-dihydroxythymine, inosine, hypoxanthine, xanthine, xanthosine, uric acid, allantoin, guanine, guanosine, nicotinamide, orotic acid, urazole, glycoluril, hydantoin, 5,5-dimethyl hydantoin, pyrrolid-2-one, pyrazol-3-one, imidazol-2-one, allopurinol, and theobromine.

5. The method of claim 1 wherein the cyclic nonpeptidyl compound has both amide and imide groups.

6. The method of claim 5 wherein the cyclic nonpeptidyl compound is selected from the group consisting of uric acid, allantoin, urazole, uridine, thymidine, uracil, thymine, 5,6-dihydroxyuracil, 5,6-dihydroxythymine, orotic acid, xanthine, xanthosine, hydantoin, 5,5-dimethylhydantoin, and theobromine.

7. The method of claim 1 wherein the cyclic nonpeptidyl compound is a natural mammalian metabolite.

8. The method of claim 7 wherein the cyclic nonpeptidyl compound is selected from the group consisting of uridine, thymidine, uracil, thymine, 5,6-dihydroxyuracil, and 5,6-dihydroxythymine, orotic acid, xanthine, xanthosine, uric acid, allantoin, and nicotinamide.

9. The method of claim 1 wherein the steps of treating the biological tissue with an aldehyde and a cyclic nonpeptidyl compound are carried out in one step.

10. The method of claim 1 wherein the treating step is carried out at a temperature greater than about 25° C.

11. The method of claim 10 wherein the treating step is carried out at a temperature of about 30–45° C.

12. The method of claim 1 wherein the biological tissue is greater than about 1 mm thick.

13. The method of claim 1 further including a step of treating the biological tissue with a reducing agent.

14. The method of claim 13 wherein the reducing agent is sodium borohydride.

15. A method for preparing a biological tissue for implantation, comprising the ordered steps of:
    (a) a first step of treating a biological tissue with an aldehyde;
    (b) a second bioprosthesis treatment step comprising treating the aldehyde-treated biological tissue with a compound in an aqueous treatment medium having a pH of less than about 7, wherein the detoxifying compound is selected from the group consisting of hypoxanthine, allantoin, barbituric acid , and urazole, the second step following the first step.

16. The method of claim 15 wherein the treating step is carried out at a temperature greater than about 25° C.

17. The method of claim 15 wherein the biological tissue is greater than about 1 mm thick.

18. The method of claim 15 wherein the biological tissue is a heart valve.

19. The method of claim 15 further including a step of treating the biological tissue with a reducing agent.

20. A method for preparing a biological tissue for implantation, comprising the ordered steps of:
    (a) a first step of treating a biological tissue with an aldehyde;
    (b) a second bioprosthesis treatment step comprising treating the biological tissue with urea, the second step following the first step.

* * * * *